(12) United States Patent
Lorenzl et al.

(10) Patent No.: US 8,093,258 B2
(45) Date of Patent: Jan. 10, 2012

(54) USE OF UROKINASE INHIBITORS FOR THE TREATMENT AND/OR PREVENTION OF NEUROPATHOLOGICAL DISEASES

(75) Inventors: Stefan Lorenzl, Neuried (DE); Wolfgang Schmalix, Gröbenzell (DE)

(73) Assignee: Wilex AG, Munich (DE)

( * ) Notice: Subject to any disclaimer, the term of this patent is extended or adjusted under 35 U.S.C. 154(b) by 789 days.

(21) Appl. No.: 11/922,774

(22) PCT Filed: Jun. 22, 2006

(86) PCT No.: PCT/EP2006/006029
§ 371 (c)(1),
(2), (4) Date: Dec. 21, 2007

(87) PCT Pub. No.: WO2006/136419
PCT Pub. Date: Dec. 28, 2006

(65) Prior Publication Data
US 2009/0069251 A1    Mar. 12, 2009

Related U.S. Application Data

(60) Provisional application No. 60/693,432, filed on Jun. 24, 2005.

(51) Int. Cl.
| | | |
|---|---|---|
| *A01N 43/54* | (2006.01) | |
| *A01N 43/42* | (2006.01) | |
| *A01N 33/18* | (2006.01) | |
| *A61K 31/517* | (2006.01) | |
| *A61K 31/47* | (2006.01) | |
| *A61K 31/04* | (2006.01) | |

(52) U.S. Cl. ............... 514/266.4; 514/309; 514/740
(58) Field of Classification Search ............ 514/266.9, 514/309, 740
See application file for complete search history.

(56) References Cited

U.S. PATENT DOCUMENTS

2004/0266766 A1 * 12/2004 Sperl ............... 514/230.5
2008/0213244 A1 *  9/2008 Sohngen ........... 424/94.64

FOREIGN PATENT DOCUMENTS

WO    WO 2004/098635    * 11/2004

OTHER PUBLICATIONS

Crisp et al. Protease nexin 1 is a potent urinary plasminogen activator inhibitor in the presence of collagen type IV. The Journal of Biological Chemistry. Dec. 6, 2002, vol. 277, No. 49, 47285-47291.*
Finckh U, van Hadeln K, Müller-Thomsen T, Alberici A, Binetti G, Hock C, Nitsch RM, Stoppe G, Reiss J, and Gal A, "Association of late-onset Alzheimer disease with a genotype of PLAU, the gene encoding urokinase-type plasminogen activator on chromosome 10q22.2," Neurogenetics, Aug. 2003 4(4), 213-217.*
Mori T, Abe T, Wakabayashi Y, Hikawa T, Matsuo K, Yamada Y, Kuwano M, Hori S. Up-regulation of urokinase-type plasminogen activator and its receptor correlates with enhanced invasion activity of human glioma cells mediated by transforming growth factor-alpha or basic fibroblast growth factor. J Neurooncol. 2000;46(2):115-23.*
International Preliminary Report on Patentability and Written Opinion of the International Searching Authority issued in International Application No. PCT/EP2006/006029, dates Jan. 10, 2008.

* cited by examiner

*Primary Examiner* — San-Ming Hui
*Assistant Examiner* — Paul Zarek
(74) *Attorney, Agent, or Firm* — McDermott Will & Emery LLP

(57) ABSTRACT

The present invention relates to methods and compositions for the treatment and/or prevention of neuropathological and/or neurodegenerative diseases. In particular, the invention delivers novel uses of inhibitors of Urokinase-type Plasminogen activator in the treatment of amyotrophic lateral sclerosis.

9 Claims, 6 Drawing Sheets

Expression of uPAR in the spinal cord of ALS-Patients

Figure 2a

Expression of uPA in the Spinal Cord of G93A-Mice

| UPAR/ β-Actin-Ratio | 30 Days (n=3) | 60 Days (n=4) | 90 Days (n=3) | 115 – 125 Days (n=5) |
|---|---|---|---|---|
| MW | 0.08 | 0.10 | 0.38 | 0.54 |
| STD | 0.05 | 0.02 | 0.10 | 0.09 |

USE OF UROKINASE INHIBITORS FOR THE TREATMENT AND/OR PREVENTION OF NEUROPATHOLOGICAL DISEASES

RELATED APPLICATIONS

This application is the U.S. National Phase under 35 U.S.C. §371 of International Application No. PCT/EP2006/006029, filed on Jun. 22, 2006, which in turn claims the benefit of U.S. Provisional Application No. 60/693,432, filed on Jun. 24, 2005, the disclosures of which Applications are incorporated by reference herein.

FIELD OF THE INVENTION

The present invention relates to methods and compositions for the treatment and/or prevention of neuropathological and/or neurodegenerative diseases. In particular, the invention delivers novel uses of inhibitors of Urokinase-type Plasminogen activator in the treatment of amyotrophic lateral sclerosis.

BACKGROUND OF THE INVENTION

The Plasminogen Activating System

The removal of blood clots from the circulation and the turnover of extracellular matrix proteins are facilitated by specialized enzymes. One very important enzyme in this setting is plasmin. Plasmin performs many functions, but it is generally accepted that its primary role is to degrade fibrin, the structural scaffold of a blood clot. The serine proteases tissue-type plasminogen activator (t-PA) and urokinase (u-PA) mediate the generation of plasmin from its inactive precursor plasminogen. Specific physiologic serine protease inhibitors, such as plasminogen activator inhibitor (PAI)-1 and PAI-2, in turn regulate the proteolytic activity of t-PA and u-PA. A specific cell surface receptor for u-PA also exists, which not only provides a means of generating localised proteolytic activity in the pericellular environment, but, with the help of adjacent transmembrane proteins, can transmit signals to the cell nucleus and influence the expression pattern of other genes.

The plasminogen activating system also actively participates in cell movement, wound healing and the metastatic spread of cancer. Finally, in addition there is evidence that the plasminogen activating system also contributes to the turnover of the extracellular matrix in the central nervous system.

Functions of the Urokinase system in the brain are also thought to be found in a various normal and pathological events, including plasticity and neurological disorders and neural and/or glial derived tumors. Urokinase and its receptor expressed in the central nervous system therefore seem to play a role in neuronal and/or (astro)glial cell migration, synaptogenesis, remodelling and reactive processes (Del Biglio et al., Int J Dev Neurosci, 1999, 17, 387-99). For example, t-PA has been shown to play a role in cognitive memory, can mediate reverse occlusion plasticity of the visual cortex, and promotes neurodegeneration.

Macrophages and microglial cells secrete plasminogen activators under various conditions. Interestingly microglial cells and macrophages proliferate and accumulate in damaged brain areas possibly triggering, besides other effects, extracellular proteolysis. Breakdown of extracellular matrix proteins involves not only secondary brain damages but also angiogenesis. Furthermore it is described that uPA in the brain may play a role in the regulation of food consumption (Miskin and Masos, J Gerontol. A Biol Sci Med Sci, 1997, 52, B118-24). Recent findings document the involvement of the urokinse system in learning-related plasticity (Meiri et al, Proc Natl. Acad Sci, 1994, 91, 3196-3200).

Besides brain tumors such as malignant gliomas, a steadily increasing percentage of the western population suffers from neuropathological diseases in which serine proteases may play a significant role.

The serine proteases seem to play an active role in the plasticity of the neuromuscular junction and therefore are major thematic approaches to neural function and dysfunction. The Plasminogen system is also involved in proteolytic processes in brain injury and inflammation and, taken together, may contribute to the pathogenesis of neurodegenerative diseases, such as, for example Alzheimers Disease, Creutzfeld-Jacob disease, amyotrophic lateral sclerosis (ALS), multiple sclerosis (MS), Parkinson Disease etc.

In multiple sclerosis (MS) lesions components of the plasminogen activator system have been characterized and seems to be concentrated on inflammatory cells. It is proposed, that the urokinase plasminogen activator increase at MS lesions may facilitate the cellular infiltration into the brain parenchyma and so support the inflammatory process in the central nervous system of MS patients (Washington et al, J. Neurosci. Re 1998, 45, 392-399).

ALS is characterized by increasing loss of motorneurons, the pathological changes of which leads to pronounced muscle weakness leading to death in most of the afflicted patients in the course of 2-5 years after diagnosis. The pathology was already described in the beginning of the 20$^{th}$ century as loss of the anterior horn cells of the spinal cord, Betz-cells in the cerebral cortex and degeneration of the corticospinal tract (Holmes, 1909).

Increased expression of the gelatinases MMP-2 and MMP-9 have been documented in the central nervous system and spinal cord of ALS patients with the highest concentration of MMP-9 being found in the thoracic and lumbal sections. Statistically significant differences compared to controls were found in the frontal and occipital cortex as well as in the entire spinal cord of ALS patients (Lim et al, J. Neurochem. 1996, 67, 251-9.). Plasma of ALS patients reveals a significant increase of MMP-2 concentrations (Beuche et al, Neuroreport, 2000, 11, 3419-22). On the other hand, the concentration of TIMP-1, an important counter regulator of MMP-2, is not altered when compared with controls. These data deliver hints of the potential pathogenic role of MMP's in ALS.

In the familial form of ALS a mutation was identified in the $Cu^{2+}/Zn^{2+}$ superoxide dismutase (SOD1)-genes (Deng et al. Science, 1993, 261, 1047-51; Rosen et al., Am J Med Genet, 1994, 51, 61-9). Additionally it was described that specific alterations in the cell-surrounding matrix is a result of a generalized proteolysis at the neuromuscular endplates (Maselli et al, Muscle Nerve, 1993, 16, 1193-203; Tsujihata et al, Muscle Nerve, 1984, 7, 243-9).

The superoxide dismutases (SOD) comprise a family of enzymes, playing a prominent protective role of cells from damage by free radicals (Fridovich J Biol Chem, 1989, 264, 7761-4). SOD1 is a soluble homodimer of 153 amino acids in length found in the cytoplasm as well as in the nucleus of numerous eucaryotic cells. The enzymes main function lies in the detoxification of the superoxide anion radicals and the concomitantly synthesized hydrogen peroxide. The resulting hydrogen peroxide is transformed into water through the action of either glutathione peroxidase or catalase (Halliwell J Neurochem, 1992, 59, 1609-23; Ann Neurol, 1992, 32, Suppl. S10-5).

An important development in the research of ALS-pathogenesis was the discovery of mutations in the SOD1 gene in 15-20% of patients diagnosed with familial ALS (Rosen et al Nature, 1993, 362, 59-62). These mutations cause the SOD1 to present reduced enzymatic activity in vivo and reduced half-life of the enzyme (Bowling et al 1993, J. Neurochem, 61, 2322-2325; Borchelt et al 1994, Proc. Natl Acad Sci USA, 91 8292-8296). The results of recent research however, move towards loss of function of the mutated enzyme. Strong arguments against the total loss of function however include the dominant inheritance of the disease and the correlation of the loss of function and the clinical course of the disease (Brown 1995, Cell, 80, 687-692). Transgenic mice, devoid of the SOD1 gene, do not have a shortened lifespan and do not develop motorneuron-related diseases (Reaume et al, 1996, Nature Genet, 13, 4347). Furthermore, mice expressing native unmutated human SOD1 in equivalent levels compared to endogenous mouse SOD also do not develop motorneuron-associated diseases. In contrast thereto transgenic mice expressing the G93A or G37R mutation of the human SOD1 gene, resulting in higher SOD1 activity or mice expressing the G85R SOD1 mutation, resulting in protein and activity concentrations comparable to endogenous levels, present progressive paraparesis and pronounced muscular atrophy (Bruijn et al 1997, Neuron, 18, 327-338; Gurney et al 1994, Science, 264, 1772-1775; Wong et al 1995, Neuron, 14, 1105-1116).

Basically two hypotheses try to explain the development of ALS due to SOD1 mutations. According to one hypothesis incorrect folding of the mutated protein leads to precipitation and formation of toxic intracellular aggregates. The second hypothesis argues that the mutated SOD1 has a changed substrate specificity, which leads to the formation of toxic side products.

Mutated SOD1 reveals varied substrate binding of the catalytic copper ion at the active site of the enzyme as well as variations in binding of other substrates. (Deng et al 1993, Science, 261, 1047-1051). In particular the substrate binding of hydrogen peroxide and peroxynitrite seems facilitated (Beckman and Crow, 1993, Biochem Soc Trans, 21, 330-334). Peroxynitrite may be transformed into the highly reactive nitronium intermediate via the catalytic copper of the mutated enzyme. This nitronium intermediate again is able to nitrate protein derived tyrosine residues. In contrast the binding of zinc is not as pronounced (Crow et al 1997, J Neurochem, 69, 1936-1944; Lyons et al, 1996, Proc. Natl. Acad. Sci. USA 93, 12240-12244). This insufficient zinc binding destabilizes the enzyme, resulting in increased nitronium ion production. This may lead to the nitration of the neurofilament light chains, which in turn prevents neurofilament triplet formation (Crow et al 1997, J Neurochem, 69, 1936-1944). This reaction is in part responsible for the cytoskeletal changes that are pathognomic for ALS (Sasaki et al, 1990, J. Neurol. Sci, 97, 233-240; Rouleau et al 1996, Ann Neuro, 39, 128-131). The concentration of 3-nitrotyrosine is increased in G37R or G93A-mutation carrying transgenic mice (Bruijn et al 1997, Neuron, 18, 327-338; Ferrante et al 1997, Ann Neurol, 42, 326-334). The detection of increased 3-nitrotyrosine concentrations was thereafter also described in the spinal cord of patients with sporadic and familial ALS (Beal et al 1997, Ann Neurol. 42, 646-654).

A further potential toxic interaction between the mutated SOD1-enzyme and hydrogenperoxide is described. It was shown in vitro that the mutated SOD1-enzyme reacts more easily with hydrogenperoxide to produce hydroxyl radicals than the native enzyme (Wiedau-Pazo et al 1996, Science, 271, 515-518; Yim et al 1997, J. Biol. Chem, 272, 8861-8863). Expression of mutated SOD1 in PC-12 cells is accompanied with a increased production of free oxygen radicals. Giving copper chelators, Bcl-2, glutathion, vitamin E and caspase inhibitors can reduce the resulting cell death (Ghadge et al, 1997, J Neurosci, 17, 8756-8766). Additionally it was shown that cultured cells carrying the mutated SOD1, but not those with wild type SOD1, present an increased rate of apoptosis (Wiedau-Pazo et al, 1996, Science, 271, 515-518; Ghadge et al 1997, J Neurosci, 17, 8756-8766). Increased production of oxygen radicals and increased protein damage through oxygen radicals was demonstrated in transgenic mice with the G93A-mutation of SOD1 (Liu et al 1998, Ann. Neurol. 44, 763-770; Andrus et al 1998, J. Neurochem, 71, 2041-2048).

G93A-transgenic mice are used as a model system for ALS. The time course of neuronal degeneration in G93A-mice is known. The onset of clinical symptoms is characterized by fine tremor of the extremities approximately at the age of 90 days, followed by paralysis and consecutively death at an age of 120-10 days (Dal Canto and Gurney, 1994, and 1995, Brain Res 676, 2540; Chiu et al, 1995, Molec. Cell. Neurosci. 6, 349-363). The earliest pathological changes manifest in mitochondrial vacuolisation in spinal motorneurons, which can be observed from day 37, initially in proximal axons and later at the age of 45 days in the cell bodies (Chiu et al 1995, Molec. Cell. Neurosci. 6, 349-363). At the age of 70 days these changes can be found in almost all motorneurons followed by a significant loss of motorneurons from the age of 90 days. The mitochondrial vacuolisation directly precedes a phase of quickly progressing amyasthenia and therefore of pathophysiological importance (Kong and Xu 1997, Soc. Neurosci Abst. 23, 1913). Expression the G93A SOD1 mutant causes in vitro a loss of the mitochondrial membrane potentials as well as an increase of the cytosolic calcium concentration (Carri et al 1997, FEBS Lett. 414, 365-368). Furthermore, the G93A-mice develop an accumulation of neurofilament in axonal spheroids (Tu et al 1996, Proc. Natl. Acad. Sci. USA 93, 3155-3160).

A connection between SOD dysfunction and MMP expression has been discussed recently. Inhibition of CuZn-SOD significantly reduced the mRNA levels of MMP-1 in dermal fibroblast (Brenneisen et al 1997, Free. Rad. Biol. Med. 22, 515-524). This study demonstrated further that this effect is coupled to the reduced production of intracellular hydrogen peroxide. By inhibiting the manganese-SOD a hydrogen peroxide driven rise in MMP-1 mRNA was found, which was partially transcription factor AP-1 mediated (Wenk et al 1999, J. Biol. Chem. 274, 25869-25876). The hydrogen peroxide production of the manganese-SOD is thought to correlate with the activation of various MMP's, such as MMP-1, MMP-3 and MMP-7 (Ranganathan et al 2001,). Furthermore hydrogen peroxide stimulates the expression of MMP's in human endothelial cells in vitro (Belkhiri et al 1997, Lab. Invest. 77, 533-539). The increase in the production of free radicals seems to be the consequence of the SOD1-muatation and can lead to an increased MMP-expression, which in turn may lead to neuronal cell death. Therefore, a close relation between the production of free oxygen radicals and the expression of MMP's may be concluded on one hand, whereas on the other hand the of MMP-expression can be initiated by a mutation of the CuZnSOD.

Despite first therapeutic approaches in amyotrophic lateral sclerosis and improved patient care through palliative treatments, the prognosis of this disease is still bad. Generally the afflicted patients die within 2-years after diagnosis. One of the main causes is the progressive amyasthenia eventually leading to paralysis of the auxiliary breathing muscles. The complex underlying pathophysiological mechanisms are only known partially. Currently there is no way of analysing the role of SOD1-mutations in the human or to perform extensive histopathological examinations on human organs at defined time points in disease progression. Interestingly the transgenic mice show pathophysiological changes and clinical findings such as progressive paraparesis and amyasthenia comparable to that found in the human disease.

The prevalence of ALS is approx. 6-8 in 100 000 people with an incidence of 1.5-2 in 100 000 people per year, with increasing tendency. Most cases are diagnosed at age 40-70, with increasing incidence at higher ages. The disease generally progresses rapidly and patients die within 2-5 years of diagnosis. The final stage of the disease is characterized by affected trunk and respiratory musculature where the patients die of respiratory insufficiency often accompanied by aspirations pneumonia.

The exact etiology of ALS is not known and a number of hypothesis try to explain the cause via immunological interferences in the neurotransmitter housekeeping, chronic intoxication, metabolic derailing, viral infections, neurotrophic factor deficiency, and disrupted DNA repair mechanisms.

Largely unanswered are the questions regarding the vulnerability of the motorneurons to the suggested pathogenic mechanisms. Maybe the expression of MMP's through activated microglia or neurons may play a role in the occurrence of apoptotic cell death.

The only known therapeutic approach comprises the treatment with riluzole, a substance that, besides others, reduces the secretion of glutamate. These treatments have been shown to reduce symptoms and to slow the progression of the physical disability. They result in prolongation of life of ca. 3 months.

The role of the Plasminogen system in the pathogenesis of ALS was studied in more detail to elucidate the concepts of synapse degeneration. ALS is a disorder, as described above, that is caused by stimuli or agents that activate a cascade of extracellularly acting proteases that disrupt synaptic connections with catastrophic repercussions on the motorneurons in the spinal cord. Animal studies and cell culture experiments have pointed towards the involvement of serine proteases to be important regulators of remodelling at the neuromuscular junction, delicately tuned by physiologic inhibitors to prevent the disruption that occurs in ALS or other forms of denervation. This may also stand for other similar synaptic degenerations in the central nervous system.

A surprising role for Urokinase was found in this debilitating disease. These findings can have important consequences for preventive or therapeutic strategies in patients with urokinase-dependant neuropathologies and/or neurodegenerative diseases.

AIM OF THE INVENTION

The present invention aims at providing therapeutics in order to improve the health of patients suffering from the consequences of urokinase-dependant neuropathological and/or neurodegenerative disease. In particular the present invention aims at providing the usage of urokinase inhibitors for the manufacture of a medicament, in order to treat patients suffering from such neuropathological and/or neurodegenerative disease. Another aim of the present invention is to provide pharmaceutical compositions for use in mentioned treatments, and yet another aim of the present invention is to provide methods for treating patients suffering from such urokinase-dependant neuropathological and/or neurodegenerative diseases.

DETAILED DESCRIPTION OF THE INVENTION

As will be shown in the following examples the present invention reveals a surprising therapeutic activity of urokinase inhibitors on the neurodegenerative disease ALS. The present invention presents the observation that the Urokinase plasminogen activator seems to have an intrinsic biological activity in neurodegenerative disease. By blocking such activity with specific and/or selective urokinase inhibitors positive therapeutic effects may be generated.

Several documents describe urokinase inhibitors which are suitable for use in the present invention. Preferred compounds and pharmaceutical compositions are described in U.S. Pat. No. 5,340,833, U.S. Pat. No. 5,550,213, U.S. Pat. No. 6,207,701, U.S. Pat. No. 6,093,731, U.S. Pat. No. 5,952,307, CH 689611, WO 00/06154, WO 00/05245, WO 00/05214, WO 01/14324, WO 99/40088, WO 99/20608, WO 99/05096, WO 98/11089, WO 01/44172, EP 1044967, EP 568289, WO 00/04954, WO 03/103644, WO 00/17158, WO 02/74756, WO 01/14324, WO 01/70204, WO 03/053999, WO 98/46632, U.S. Pat. No. 6,586,405, EP 1 182 207 A, WO 02/14349, WO 00/05245, WO 03/048127, WO 03/076391, WO 01/96286; WO 2004/103984, the disclosure of which is incorporated herein by reference.

Preferred urokinase inhibitors are described in US2004/0266766, the disclosure of which is incorporated herein by reference, i.e. compounds of the general formula I

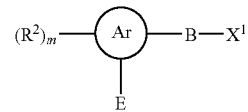

in which
Ar denotes an aromatic or heteroaromatic ring system,
E denotes

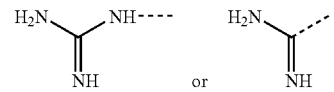

or Ar and E together form a residue

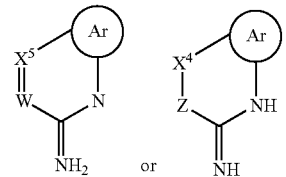

in which Z can be O, NH or C=O and $X^1$ can be C=O, NH or $CH_2$ and W can be N, $CR^3$ or $CR^6$ and $X^5$ can be CH, $CR^3$, $CR^6$ or N,
B denotes —$SO_2$—, —$CR^3{}_2$—, —$NR^3$— or —NH—,
$X^1$ denotes $NR^{13}R^4$, $OR^3$, $SR^3$, $COOR^3$, $CONR^3R^4$ or $COR^5$, $R^1$ denotes H, an optionally substituted alkyl, alkenyl, alkinyl, aryl, heteroaryl residue or $COOR^3$, $CONR^3R^4$ or $COR^5$, $R^2$ denotes halogen, $C(R^6)_3$, $C_2(R^6)_5$, $OC(R^6)_3$ or $OC_2(R^6)_5$, $R^3$ denotes H or any organic residue, $R^{13}$ denotes a group of the general formula (IIa) or (IIb),

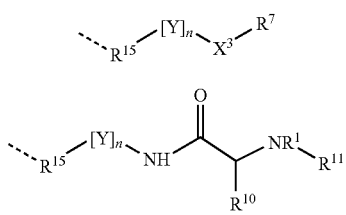

$X^2$ denotes NH, $NR^4$, O or S, $X^3$ denotes NH, $NR^4$, O, S, CO, COO, CONH or $CONR^4$, Y denotes $C(R^8)_2$, NH or $NR^3$, $R^4$ denotes H or a branched or unbranched, optionally substituted alkyl, alkenyl or alkinyl residue, $R^5$ denotes H, an alkyl, alkenyl, alkinyl carboxy-alkyl, carboxy-alkenyl, carboxyl-alkinyl, carboxy-aryl, carboxy-heteroaryl, —(CO)$NR^3R^4$ or —COO—$R^3$ in which the alkyl, aryl and heteroaryl residues can optionally be substituted, $R^6$ is in each case independently H or halogen and in particular F, $R^7$ denotes H or an optionally substituted alkyl, alkenyl, alkinyl, aryl or heteroaryl residue or —$COR^9$, $R^8$ in each case independently denotes H, or a branched or unbranched, optionally substituted alkyl, alkenyl, alkinyl, aryl, heteroaryl, aralkyl, alkylaryl, heteroaralkyl residue or/and a substituted or unsubstituted bicyclic or polycyclic residue, $R^9$ denotes H or a branched or unbranched, optionally substituted alkyl, alkenyl, alkinyl, aryl or/and heteroaryl residue, $R^{10}$ denotes a residue $(C(R^1)_2)_o$—$X^3R^5$, $R^{11}$ denotes H, a carbonyl residue —CO—$R^{12}$, a carbonamido residue —$CONR^{12}_2$, an oxycarbonyl residue —COO—$R^{12}$ or particularly preferably a sulfonyl residue —$SO_2R^{12}$, $R^{12}$ denotes H, a branched or unbranched, substituted or unsubstituted alkyl, alkenyl, alkinyl, aryl or heteroaryl residue or a substituted or unsubstituted cyclic alkyl residue or a substituted or unsubstituted aralkyl, alkylaryl or heteroaralkyl residue or a substituted or unsubstituted bicyclic or polycyclic residue, $R^{15}$ represents C=$X^2$, $NR^3$ or $CR^3_2$, n is an integer from 0 to 2, m is an integer from 0 to 5, o is an integer from 1 to 5, p is an integer from 1 to 5, or salts of these compounds More preferred urokinase inhibitors are compounds of the general formula III

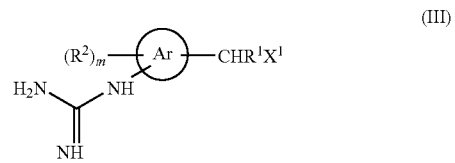

in which

Ar denotes an aromatic or heteroaromatic ring system, $X^1$ denotes $NR^{13}R^4$, $OR^3$, $SR^3$, $COOR^3$, $CONR^3R^4$ or $COR^5$, $R^1$ denotes H, an optionally substituted alkyl, alkenyl, alkinyl, aryl, heteroaryl residue or $COOR^3$, $CONR^3R^4$ or $COR^5$, $R^2$ denotes halogen, $C(R^6)_3$, $C_2(R)_5$, $OC(R^6)_3$ or $OC_2(R^6)_5$, $R^3$ denotes H or any organic residue, $R^{13}$ denotes a group of the general formula (IVa) or (IVb),

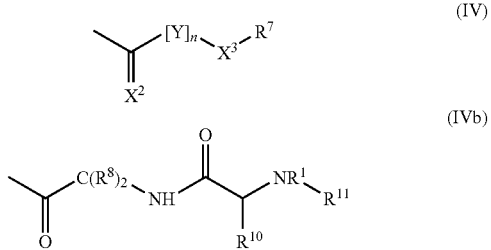

$X^2$ denotes NH, $NR^4$, O or S, $X^3$ denotes NH, $NR^4$, O, S, CO, COO, CONH or $CONR^4$, Y denotes $C(R^8)_2$, NH or $NR^3$, $R^4$ denotes H or a branched or unbranched, optionally substituted alkyl, alkenyl or alkinyl residue, $R^5$ denotes H, an alkyl, alkenyl alkinyl, carboxy-alkyl, carboxy-alkenyl, carboxyl-alkinyl, carboxy-aryl carboxy-heteroaryl, —(CO)$NR^3R^4$ or COO—$R^3$ in which the alkyl, aryl and heteroaryl residues can optionally be substituted, $R^6$ is in each case independently H or halogen and in particular F, $R^7$ denotes H or an optionally substituted alkyl, alkenyl, alkinyl, aryl or heteroaryl residue or —$COR^9$, $R^8$ in each case independently denotes H, halogen, or a branched or unbranched, optionally substituted alkyl, alkinyl, aryl, heteroaryl residue or/and $(CH_2)_m$—OH, $R^9$ denotes H or a branched or unbranched, optionally substituted alkyl, alkenyl, alkinyl, aryl or/and heteroaryl residue, $R^{10}$ denotes a residue $(C(R^1)_2)_o$—$X^3R^5$, $R^{11}$ denotes H, a carbonyl residue —CO—$R^{12}$, an oxycarbonyl residue —COO—$R^{12}$ or particularly preferably a sulfonyl residue —$SO_2R^{12}$, $R^{12}$ denotes a branched or unbranched, substituted or unsubstituted alkyl, alkenyl, alkinyl, aryl or heteroaryl residue or a substituted or unsubstituted cyclic alkyl residue or a substituted or unsubstituted aralkyl, alkylaryl or heteroaralkyl residue or a substituted or unsubstituted bicyclic or polycyclic residue, n is an integer from 0 to 2, m is an integer from 0 to 5, o is an integer from 1 to 5, or salts of these compounds The compounds can be present as salts, preferably as physiologically acceptable acidic salts e.g. as salts of mineral acids, particularly preferably as hydrochlorides or as salts of suitable organic acids. The guanidinium group can optionally carry protective functions that can be preferably cleaved under physiological conditions. The compounds can be present as optically pure compounds or as mixtures of enantiomers or/and diastereoisomers.

The ring system Ar preferably contains 4 to 30 and in particular 5 to 10 C-atoms. In the compounds of the general formula (I) or (III), Ar is preferably an aromatic or heteroaromatic ring system with one ring. Compounds are also preferred in which Ar and E together form a bicyclic system. Heteroaromatic systems preferably contain one or more O, S or/and N atoms. A preferred aromatic ring system is a benzene ring; preferred heteroaromatic ring systems are pyridinyl, pyrimidinyl or pyrazinyl, especially with nitrogen at position 2. Preferred bicyclic ring systems are those with nitrogen or oxygen at positions Z or W. Ar is most preferably a benzene ring.

Compounds with the following structural elements are particularly preferred

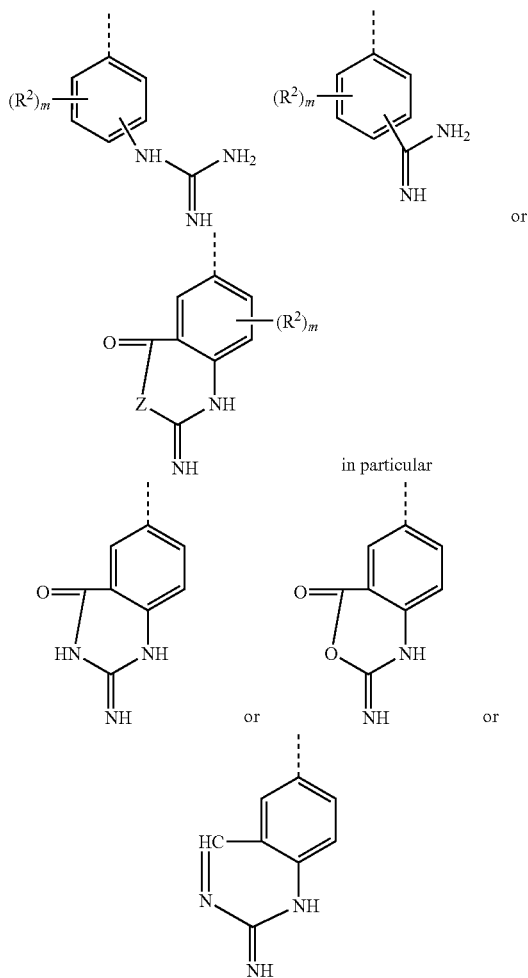

in particular or

In the compounds of the general formula (I) or (III), the substituents B e.g. $CHX^1R^1$ and E, e.g. $NHC(NH)NH_2$ (guanidino) or $NH_2CNH$ (amidino) in the ring system Ar are preferably in the meta or para position and particularly preferably in the para position relative to one another. Moreover, Ar can contain one or more additional substituents $R^2$ that are different from hydrogen. The number of substituents $R^2$ is preferably 0, 1, 2 or 3, particularly preferably 0 or 1 and most preferably 0. $R^2$ can denote halogen, $C(R^6)_3$, $C_2(R^6)_5$, $OC(R^6)_3$ or $OC_2(R^6)_5$ in which case $R^6$ is in each case independently H or halogen and in particular F. Preferred examples of $R^2$ are halogen atoms (F, Cl, Br or I), $CH_3$, $CF_3$, OH, $OCH_3$ or $OCF_3$.

The compounds according to the invention contain a guanidino group and are characterized by a high selectivity. For this reason E is often preferably $-NH-C(NH)-NH_2$.

The substituent B in formula (I) or $-CHX^1R^1$ in formula (III) is important for the inhibitor activity. B is preferably selected from $-SO_2-$, $-NR^3-$, $-NH-$ or/and $-CR^3_2-$, in particular $CR^1_2-$.

$R^1$ can be H or an optionally substituted alkyl, alkenyl, alkinyl, aryl or/and heteroaryl residue or $COOR^3$, $CONR^3R^4$ or $COR^5$. $R^1$ is most preferably H.

If not stated otherwise an alkyl residue as used herein is preferably a straight-chained or branched $C_1$-$C_{30}$ alkyl group, preferably a $C_1$-$C_{10}$ alkyl group, in particular a $C_1$-$C_4$ alkyl group or a $C_3$-$C_{30}$ cycloalkyl group in particular a $C_3$-$C_8$ cycloalkyl group that can for example be substituted with $C_1$-$C_3$ alkoxy, hydroxyl, carboxyl, amino, sulfonyl, nitro, cyano, oxo or/and halogen and also with aryl or heteroaryl residues. If not stated otherwise, alkenyl and alkinyl residues are herein preferably $C_2$-$C_{10}$ groups, in particular $C_2$-$C_4$ groups which can optionally be substituted as previously stated. Aryl and heteroaryl residues can for example be substituted with $C_1$-$C_6$ alkyl, $C_1$-$C_3$ alkoxy-hydroxyl, carboxyl, sulfonyl, nitro, cyano or/and oxo. Aryl and heteroaryl residues preferably contain 3 to 30, in particular 4 to 20, preferably 5 to 15 and most preferably 6 to 10 C atoms.

$X^1$ preferably represents $NR^{13}R^4$.

$R^3$ can denote H or any organic residue. The organic residue is in particular a residue with 1 to 30 carbon atoms. This residue can be saturated or unsaturated, linear, branched or cyclic and optionally contain substituents. In a preferred embodiment $R^3$=H especially in the group $B=-CR^3_2-$.

In a particularly preferred embodiment B represents the group $-SO_2-$ so that they are sulfo compounds. This $SO_2$ group is isosteric to the $CH_2$ group. Replacing the $CH_2$ group by the isosteric $SO_2$ group enables the formation of additional H bridges to the NH groups of Gly 193, Asp 194 and Ser 195 of urokinase which further improves the inhibitory activity (cf. FIG. 1).

$R^{13}$ represents a group of formula (IIa) or (IIb)

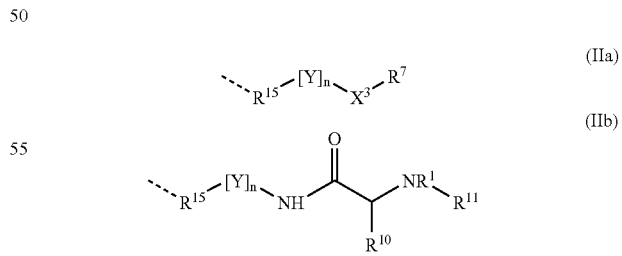

In formula (IIa) $R^{15}$ denotes $C=X^2$ or $CR^3$ where $X^2$ is NH, $NR^4$, O or S and $X^3$ is NH, $NR^4$, O, S, CO, COO, CONH or $CONR^4$. Y is $C(R^8)_2$, NH or $NR^3$. $R^4$ in turn denotes H or a branched or unbranched, optionally substituted alkyl, alkenyl or alkinyl residue. $R^7$ denotes H or an optionally substituted alkyl, alkenyl, alkinyl, aryl or heteroaryl residue or $-COR^9$ where $R^9$ in turn represents H or a branched or unbranched, optionally substituted alkyl, alkenyl, alkinyl, aryl or/and heteroaryl residue.

$R^{13}$ is preferably a group of formula (IIb).

In addition $R^{13}$ preferably represents a group of formula (VIa) or (VIb) especially in compounds of formula (III).

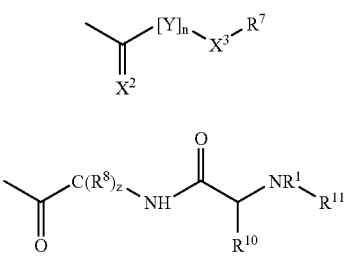

(IVa)

(IVb)

In formula (IVa) $X^2$ preferably denotes NH, $NR^4$, O or S, in particular O and $X^3$ represents NH, $NR^4$, O, S, CO, COO, CONH or $CONR^4$. Y represents $C(R^8)_2$, NH or $NR^3$. $R^4$ in turn denotes H or a branched or unbranched, optionally substituted alkyl, alkenyl or alkinyl residue. $R^7$ denotes H or an optionally substituted alkyl, alkenyl, alkinyl, aryl or heteroaryl residue or —$COR^9$, where $R^9$ in turn represents H or a branched or unbranched, optionally substituted alkyl, alkenyl, alkinyl, aryl or/and heteroaryl residue. In compounds of formula (III) $R^{13}$ preferably represents a group of formula (IVb).

$R^8$ is preferably hydrogen or $(CH_2)_m$—OH and particularly preferably H. $R^{10}$ represents a residue $(CRR^1)_2)_o$—$X^3R^5$. In this case $R^1$ is particularly preferably hydrogen, $X^3$ is particularly preferably oxygen, $R^5$ is particularly preferably hydrogen and o is particularly preferably 1.

$R^{11}$ particularly preferably represents a sulfonyl residue —$SO_2$—$R^{12}$ where $R^{12}$ is preferably an aralkyl residue and in particular a benzyl residue. In a particularly preferred embodiment the benzyl residue is substituted at the meta and/or para position with halogen and most preferably with Cl. In another preferred embodiment $R^{12}$ is an adamantyl or camphor residue.

$R^{15}$ particularly preferably represents a carbonyl residue —CO, amine residue —$NR^3$— or/and alkyl residue —$CR^3_2$, preferably —$CR^1_2$— and most preferably —$CH_2$—.

Compounds in which $R^{15}$ represents $CH_2$ are characterized by a particularly simple synthesis. Since this position is not involved in the formation of hydrogen bridges with urokinase, a $CH_2$ group may be present instead of a carbonyl without being associated with a loss in inhibitory activity.

Compounds are also preferred which contain a non-natural amino acid as a building block especially for the residue $R^{10}$. Furthermore aza compounds are preferred containing the group NH—NH in which for example Y=NH and n=1 (compounds of formula IIb).

Other particularly preferred compounds are bisulfonamides i.e. compounds which contain the element —$SO_2$—NH twice. Compounds are also preferred in which $R^{13}$ represents a group of formula IIb and Y represents —$C(R^8)_2$— where $R^8$ once represents H and once represents a residue which contains an aromatic group and in particular —$CH_2$—$CH_2$—$C_6H_5$.

Compounds are also preferred in which $X^1$ denotes

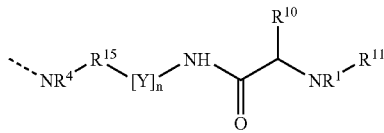

The following compounds are most preferred: N-[2-(4-guanidino-benzenesulfonyl-amino)-ethyl]-3-hydroxy-2-phenylmethanesulfonylaminopropionamide hydrochloride, Bz-$SO_2$-(D)-Ser-(Aza-Gly)-4-guanidino-benzylamide hydrochloride or N-(4-guanidino-benzyl)-2-(3-hydroxy-2-phenylmethane-sulfonylaminopropionylamino)-4-phenyl-butyramide hydrochloride and N-[(4-guanidino-benzylcarbamoyl)-methyl]-3-hydroxy-2-phenylmethanesulfonylaminopropionamide (see also FIG. 2: WX-508). Further preferred compounds are 3-nitrobenzyl-sulfonyl-(D)-Ser-Gly-(4-guanidinobenzyl)amide hydrochloride (WXC-316), 3-chlorobenzyl-sulfonyl-(D)-Ser-Gly-(4-guanidinobenzyl)amide hydrochloride (WXC-318), 4-chlorobenzyl-sulfonyl-(D)-Ser-Gly-(4-guanidinobenzyl) amide hydrochloride (WXC-340), benzylsulfonyl-(D)-Ser-Ala-(4-guanidinobenzyl)amide hydrochloride (WX-532), 4-chlorobenzylsulfonyl-(D)-Ser-N-Me-Ala-(4-guanidinobenzyl)amide (WX-582) or benzylsulfonyl-(D)-Ser-N-Me-Gly-(4-guanidinobenzyl)amide (WX-538).

An especially preferred compound is 4-chlorobenzyl-sulfonyl-(D)-Ser-Gly-(4-guanidinobenzyl)amide, or a pharmaceutically acceptable salt thereof, e.g. the hydrochloride salt (WX-C340).

Thus in a first aspect the invention relates to the use of Urokinase inhibitors in the preparation of a pharmaceutical composition for the treatment of neuropathological and/or neurodegenerative diseases, particularly ALS, Multiple Sclerosis, Morbus Parkinson, Morbus Alzheimer and bacterial meningitis.

In particular the present invention provides the use of Urokinase inhibitors for the manufacture of a medicament for the treatment and/or prophylaxis of disorders associated with urokinase-dependant neuropathologies and/or neurodegeneration.

The term "urokinase inhibitor" also encompasses optical isomers of compounds, mixtures of optical isomers, pharmaceutically acceptable salts, solvates or derivatives, e.g. pharmaceutically acceptable derivatives such as esters or amides. Further, the term encompasses prodrugs which as such are not urokinase inhibitors but which are converted into active urokinase inhibitors upon administration.

The urokinase inhibiting activity may be determined as described in US2004/0266766, for example.

The urokinase inhibitor may be administered alone or preferably formulated as a pharmaceutical composition. Furthermore the active compound may be administered in combination with other known pharmaceutical compounds used for the treatment of neuropathological and/or neurodegenerative diseases. For example, the urokinase inhibitor may also be administered in combination with superoxide dismutase/catalase mimetics and/or other synthetic or non-synthetic catalytic scavengers, for example the compounds EUK-8, EUK.134, EUK-189, EUK-207 for the treatment of neuropathological and/or neurodegenerative diseases.

The pharmaceutical preparations can be administered to humans and animals topically, orally, rectally or parenterally e.g. intravenously, subcutaneously, intramuscularly, intraperitoneally, sublingually, nasally or/and by inhalation e.g. in the form of tablets, dragees, capsules, pellets, suppositories, solutions, emulsions, suspensions, liposomes, inhalation sprays or transdermal systems such as plasters.

The invention provides a method for urokinase inhibition in living organisms especially in humans by administration of an effective amount of at least one compound of the general formula (I). The dose of the compound is usually in the range of 0.01 to 100 mg/kg body weight per day. The duration of treatment depends on the severity of the disease and can range from a single administration to a treatment lasting several weeks or even many months which can optionally be repeated at intervals.

DESCRIPTION OF THE FIGURES

FIG. 2a: PCR analysis of uPAR expression in the spinal cord of G93A SOD1 mutant mice. Abbreviations: MW=mean; STD=Standard Deviation. The level of uPAR increases during disease progression in transgenic ALS mice.

Figure 1:
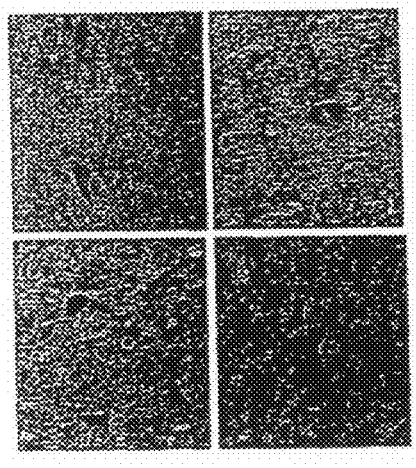
FIG. 1: 1A-1D shows the expression of the Urokinase plasminogen activator receptor (uPAR) in spinal cord sections of ALS patients after Immunohistochemical staining with ant-uPAR antibodies. The arrows highlights stained neurons. Staining seems to be more prominent in the cell membrane. A) and B) show sections of spinal cord of control cases. No immunoreactivity is seen in spinal cord neurons. In C) and D) spinal cord sections of ALS cases are seen. In these cases the uPAR antibody weakly labelled singular neurons.
Figure 2B:
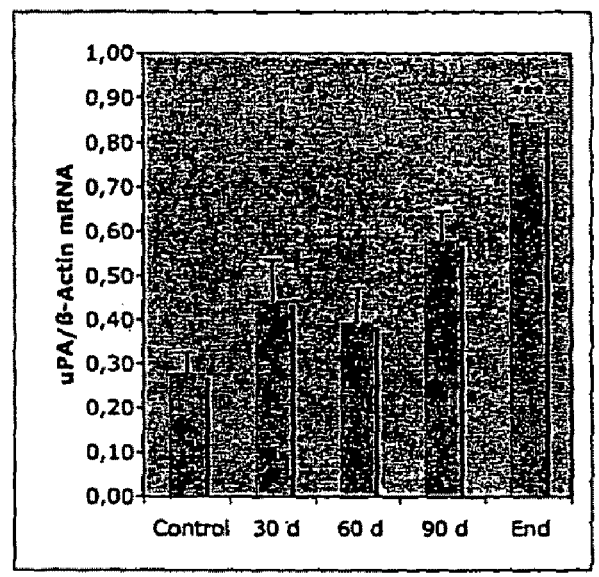
FIGS. 2b and 2c: Expression profile of uPA- and uPAR-mRNA in spinal cords of G93A mice during different times of age (d=days, End=endstage, Control=120 days old non-transgenic littermate). At the age of 90 days a significant increased expression of uPA- and uPAR-mRNA can be seen in the spinal cord of G93A mice as compared to the controls. $*p<0.05$; $***p<0.001$.
Figure 2C:
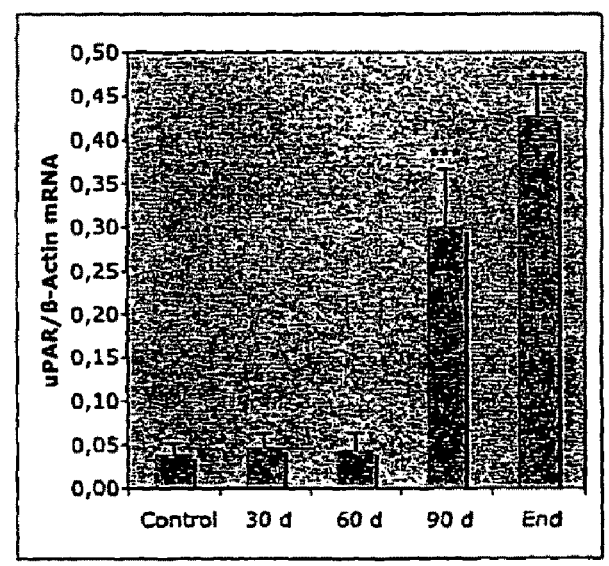
Figure 3A:
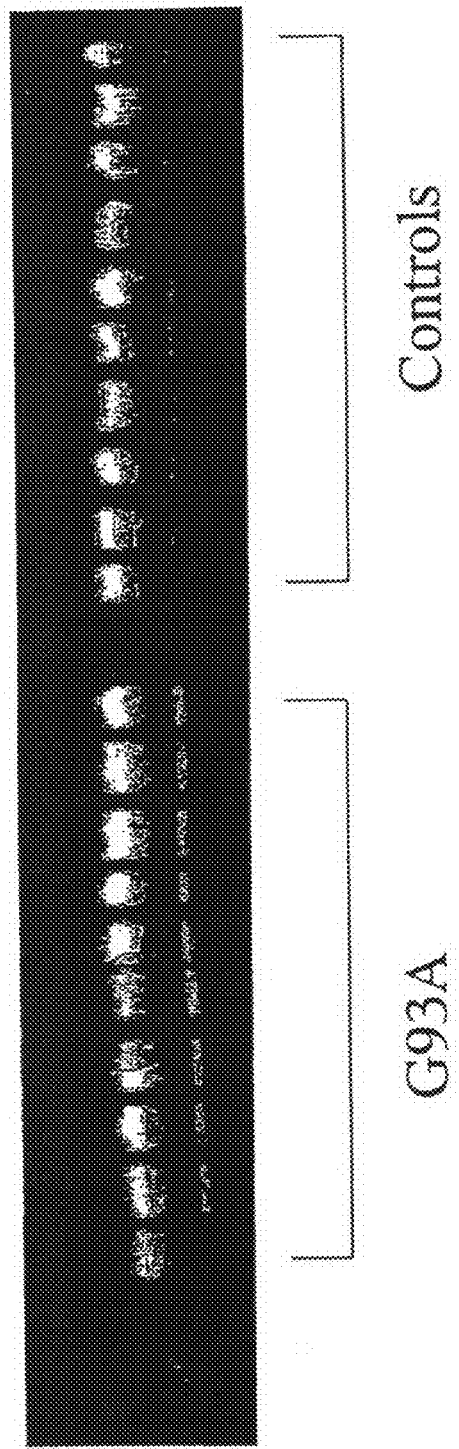
FIG. 3a: PCR analysis of Urokinase plasminogen activator (uPA) expression in the spinal cord of G93A SOD1 mutant mice.
Figure 3B:
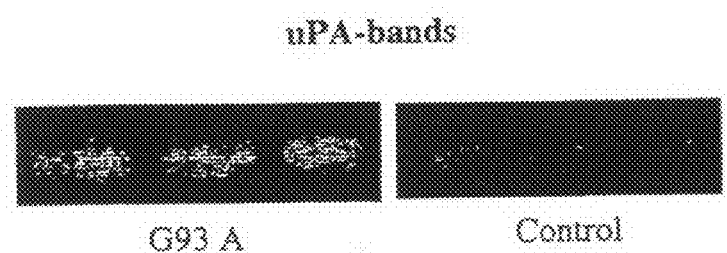
FIGS. 3b and 3c: Representative examples of zymography of spinal cord homogenates (b) and the optical band densities (c). The uPA dependent plasminogen activation significantly increased in G93A mice compared to the controls. $***p<0.001$.
Figure 3C:
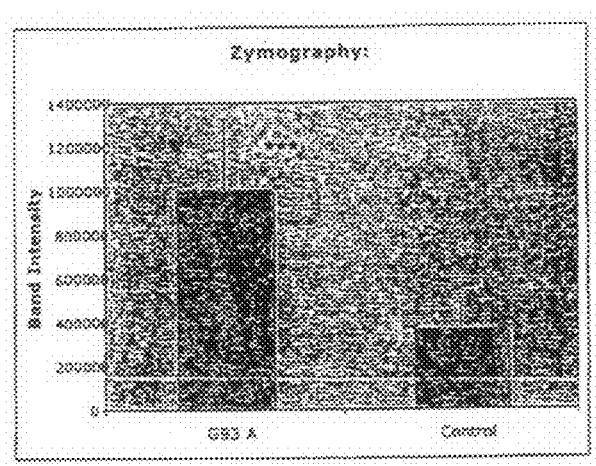

Kaplan-Meyer-Analysis, G93A-ALS-model: Comparison of the survival of control group animals (N=42) with animals treated with 10 mg/kg WX-C340 i.p. Daily (treatment start day 30, n=18).

EXAMPLES

1. Survival Analysis

FALS mice (G93A) begin to show behavioral symptoms at about 90 days of age while G85R mice develop symptoms at about 8 months of age. The initial symptoms is a high frequency resting tremor. This progresses to gait abnormalities and uncoordinated movements. Later the mice begin to show paralysis of the hind limbs, eventually progressing to paralysis of the forelimbs and finally to complete paralysis. Animals were sacrificed when they were unable to roll over within 10 seconds of being pushed on their side. This time point is taken as the time of death.

2. Behavioral Testing-Rotorod

Mice were given two days to get acquainted with the rotorod apparatus (Columbus Instruments, Columbus, Ohio) before testing. Testing was initialised with the animals trying to stay on a rod that is rotating at 1 rpm. In the following trials the speed was increased by 1 rpm every 10 seconds until the animal falls off. Each mouse had three trials. The speed of rod rotation at which the mouse falls off was used as the measure of competency on this task. Animals were tested every other day until they were unable to perform the task.

3. Zymography

Caseinolytic (uPA) activity was measured in tissue specimens of transgenic mice by zymography. Proteinases with caseinolytic activity was identified by SDS-PAGE in 15% polycrylamide gels containing 1 mg/ml casein (Sigma). 16 µl of sample (with equal protein concentration) was diluted with 4 µl of sample buffer containing 62.5 mM Tris-HCL, 2% SDS, 25% glycerol, 0.01% bromophenol blue and subjected to electrophoresis at 25 mA for 1 h 30 min at 4° C. After electrophoresis the gels were washed twice for 30 min in 2% Triton X-100 (VWR Scientific products, West Chester, Pa.) and incubated for 20 h in incubation buffer (50 mM Tris base, 5 mM $CaCl_2$, 1 µM $ZnCl_2$, 0.01% sodium azide, pH 7.5) at 37° C. After incubation gels were fixed in 20% trichloro acetic acid (Sigma T4885) for 30 min and stained in 0.5% Coomassie brilliant blue (Sigma B-7920) for 90 min. After staining, gels were de-stained in 35% ethanol and 10% acetic acid for 60 min. Gelatinolytic activity was visible as clear bands on a blue background. Standard protein markers (Bio-Rad) were used to identify the caseinolytic bands on the gels.

4. RT-PCR

Total RNA was extracted from tissue samples using a two-step protocol. Frozen tissue was pulverized and RNA prepared in the first step by using the guanidinium thiocyanide method according to Chomczynski and Sacchi (Chomczynski and Sacchi, 1987). After precipitation with isopropanol, the RNA was redissolved in lysis buffer from the RNeasy mini kit (Qiagen, Hilden, Germany) and prepared according to the manufacturer's instructions. Total RNA (15 µg) was separated in a 1.4% denaturating agarose gel containing 2.2 mol/L formaldehyde, transferred overnight by capillary blot onto Duralton ultraviolet membrane (Stratagene, La Jolla, Calif.) and cross-linked with an ultraviolet cross-linker (Stratagen). The membranes were hybridised for 1 hour in Quick Hyb (Stratagene) at 68° C. with randomly primed $^{32}P$-labeled cDNA along with DNA probes.

The membranes were washed twice for 15 min at 60° C. in 2× standard saline citrate, 0.1% sodium dodecyl sulfate (SDS), and finally in 0.1% standard saline citrate and 0.1% SDS for 30 min and exposed to Biomax MR film (Kodak) with intensifying screen for 18 to 48 h at −80° C. The mRNA levels were quantified by densitometric analysis using Fluor-S Multimager system (BioRad) and Quantity one version 4.1.0. (BioRad). GAPDH is used as loading control.

The total cellular RNA was extracted as described above. A reverse transcription system (Promega, Madison, Wis.) was used to generate the first cDNA strand according to the instructions of the manufacturer. Subsequently, a polymerase chain reaction (PCR) was performed using 2 µl of the reverse transcription reaction and Taq polymerase (high fidelity; Boehringer Mannheim, Germany) with the following thermocycle parameters: 4 minutes at 94° C.; 31 cycles of 45 seconds at 94° C., 1 min at 55° C., and 1 min at 72° C.; and 7 min at 72° C.

GAPDH primers were used as a loading control. As a negative control, reverse transcription-PCR was carried out in the absence of RNA. The amplification products were separated in 1.5% agarose gels.

5. Immunohistochemistry of uPAR in Spinal Cord Tissue from Patients with ALS and Controls To assess the anatomical distribution of uPAR in patients with ALS and controls, immunohistochemistry was performed using anti uPAR antibody IIIF10. Human brain tissue from 5 neuropathologically confirmed cases of clinical and neuropathological defined ALS patients and 3 control patients was studied. Microscopic examination was carried out using 10 μm sections from formalin-fixed, paraffin-embedded tissue blocks taken from various cortical areas (frontal, parietal, hippocampus), the brain stem and thoracic and lumbar spinal cord specimens. The sections were incubated with a blocking solution containing 20% normal goat serum (Vector, Burlingham, Calif., USA) and reacted with uPAR antibody at the recommended dilutions. Immunohistochemistry was performed using the avidin-biotin technique (Vector) and the nuclei were counterstained with haematoxylin/eosin. As a negative control, sections were incubated without primary antibody.

6. Treatment with uPA Inhibitor WX-C340

Figure 4:
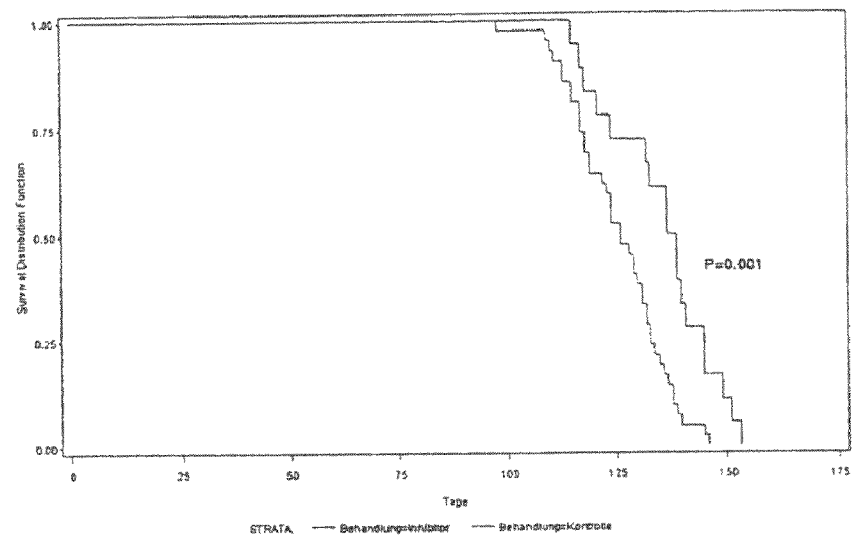
FIG. 4: Results of treatment of G93A mutant mice with the uPA-inhibitor WX-C340.

Administration of 10 mg WX-C340 i.p. daily to FALS mice delays the progression of disease (onset of paralysis of the front legs) and significantly improves the survival of the animals as shown in FIG. 4.

The invention claimed is:

1. A method for inhibiting the activity of urokinase in a patient having a neurodegenerative disease comprising administering to the patient an inhibitory sufficient amount of a urokinase inhibitor of the general formula I $$(R^2)_m - Ar(E) - B - X^1$$

in which
Ar denotes an aromatic or heteroaromatic ring system,
E denotes $$H_2N-C(NH)-NH--- \text{ or } H_2N-C(NH)-$$

or Ar and E together form a residue in which Z can be O, NH or C=O and $X^4$ can be C=O, NH or $CH_2$ and W can be
N, $CR^3$ or $CR^6$ and $X^5$ can be CH, $CR^3$, $CR^6$ or N,
B denotes $-SO_2-$, $-CR^3_2-$, $-NR^3-$ or $-NH-$,
$X^1$ denotes $NR^{13}R^4$, $OR^3$, $SR^3$, $COOR^3$, $CONR^3R^4$ or $COR^5$,
$R^1$ denotes H, an optionally substituted alkyl, alkenyl, aklinyl, aryl, heteroaryl residue or $COOR^3$, $CONR^3R^4$ or $COR^5$
$R^2$ denotes halogen, $C(R^6)_3$, $C_2(R^6)_5$, $OC(R^6)_3$ or $OC_2(R^6)_5$,
$R^3$ denotes H,
$R^{13}$ denotes a group of the general formula (IIa) or (IIb), $$\cdots R^{15} - [Y]_n - X^3 - R^7 \quad (IIa)$$

$$\cdots R^{15} - [Y]_n - NH - C(O) - CH(R^{10}) - NR^1 R^{11} \quad (IIb)$$

$X^2$ denotes NH, $NR^4$, O or S,
$X^3$ denotes NH, $NR^4$, O, S, CO, COO, CONH or $CONR^4$,
Y denotes $C(R^8)_2$, NH or $NR^3$,
$R^4$ denotes -H or a branched or unbranched, optionally substituted alkyl, alkenyl or alkinyl residue,
$R^5$ denotes H, an alkyl, alkenyl, alkinyl, carboxy-alkyl, carboxy-alkenyl, carboxyl-alkinyl, carboxy-aryl, carboxy-heteroaryl, $(CO)NR^3R^6$ or $-COO-R^3$ in which the alkyl, aryl and heteroaryl residues can optionally be substituted,
$R^6$ is in each case independently H or halogen and in particular,
$R^7$ denotes H or a an optionally substituted alkyl, alkenyl, alkinyl, aryl or heteroaryl residue or $-COR^9$,
$R^8$ in each case independently denotes H, or a branched or unbranched, optionally substituted alkyl, alkenyl, alkinyl, aryl, heteroaryl, aralkyl, alkylaryl, heteroaralkyl residue or/and a substitute or unsubstituted bicyclic or polycyclic residue,
$R^9$ denotes H or a branched or unbranched, optionally substituted alkyl, alkenyl, alkinyl, aryl or/and heteroaryl residue,
$R^{10}$ denotes a residue $(C(R^1)_2)_o - X^3 R^5$
$R^{11}$ denotes $H[_1]$ a carbonyl residue $-CO-R^{12}$, B carbonamido residue $-CONR^{12}$, an oxycarbonyl residue $-COO-R^{12}$ or particularly preferably a sulfonyl residue $-SO_2R^{12}$,
$R^{12}$ denotes H, a branched or unbranched, substituted or unsubstituted alkyl, alkenyl, alkinyl, aryl or heteroaryl residue or a substituted or unsubstituted cyclic alkylresided or a substituted or unsubstituted aralkyl, alkylaryl or heteroaralkyl residue or a substituted or unsubstituted bicyclic or polycyclic residue,
$R^{15}$ represents $C=X^2$, $NR^3$ or $CR^3_2$,
n is an integer from 0 to 2,
m is an integer from 0 to 5,
o is an integer from 1 to 5,
or salts of these compounds.

2. The method of claim 1, wherein the patient is a human.

3. The method of claim 1 in which the urokinase inhibitor is 4-chlorobenzyl-sulfonyl-(D)-Ser-Gly-(4-guanidinobenzyl)amide hydrochloride or any other salt thereof.

4. The method of claim 1 wherein the neurodegenerative disease is amyotrophic lateral sclerosis.

5. The method of claim 1 wherein the urokinase inhibitor is administered to the patient in an adjuvant protocol.

6. The method according to claim 1 wherein the neurodegenerative disease is selected from Multiple sclerosis, Morbus Parkinson and Morbus Alzheimer.

7. A method for inhibiting the activity of urokinase in a patient having bacterial meningitis comprising administering to the patient an inhibitory sufficient amount of a urokinase inhibitor of the general formula I

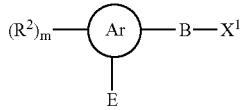

in which
Ar denotes an aromatic or heteroaromatic ring system,
E denotes

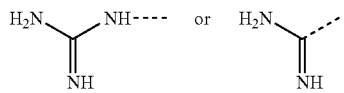

or Ar and E together form a residue

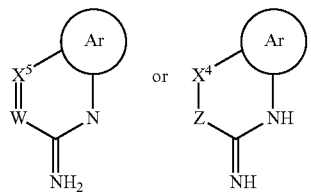

in which Z can be O, NH or C=O and $X^4$ can be C=O, NH or $CH_2$ and W can be
N, $CR^3$ or $CR^6$ and $X^5$ can be CH, $CR^3$, $CR^6$ or N,
B denotes —$SO_2$—, —$CR^3{}_2$—, —$NR^3$— or —NH—,
$X^1$ denotes $NR^{13}R^4$, $SR^3$, $COOR^3$, $CONR^3R^4$ or $COR^5$,
$R^1$ denotes H, an optionally substituted alkyl, alkenyl, aklinyl, aryl, heteroaryl residue or $COOR^3$, $CONR^3R^4$ or $COR^5$
$R^2$ denotes halogen, $C(R^6)_3$, $C_2(R^6)_5$, $OC(R^6)_3$ or $OC_2(R^6)_5$,
$R^3$ denotes H,
$R^{13}$ denotes a group of the general formula (IIa) or (IIb),

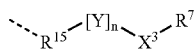 (IIa)

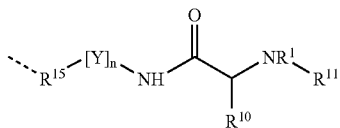 (IIb)

$X^2$ denotes NH, $NR^4$, O or S,
$X^3$ denotes NH, $NR^4$, O, S, CO, COO, CONH or $CONR^4$,
Y denotes $C(R^8)_2$, NH or $NR^3$,
$R^4$ denotes -H or a branched or unbranched, optionally substituted alkyl, alkenyl or alkinyl residue,
$R^5$ denotes H, an alkyl, alkenyl, alkinyl, carboxy-alkyl, carboxy-alkenyl, carboxyl-alkinyl, carboxy-aryl, carboxy-heteroaryl, $(CO)NR^3R^6$ or —COO—$R^3$ in which the alkyl, aryl and heteroaryl residues can optionally be substituted,
$R^6$ is in each case independently H or halogen and in particular,
$R^7$ denotes H or a an optionally substituted alkyl, alkenyl, alkinyl, aryl or heteroaryl residue or —$COR^9$,
$R^8$ in each case independently denotes H, or a branched or unbranched, optionally substituted alkyl, alkenyl, alkinyl, aryl, heteroaryl, aralkyl, alkylaryl, heteroaralkyl residue or/and a substitute or unsubstituted bicyclic or polycyclic residue,
$R^9$ denotes H or a branched or unbranched, optionally substituted alkyl, alkenyl, alkinyl, aryl or/and heteroaryl residue,
$R^{10}$ denotes a residue $(C(R^1)_2)_o$—$X^3R^5$
$R^{11}$ denotes H[₁] a carbonyl residue —CO—$R^{12}$, B carbonamido residue —$CONR^{12}$, an oxycarbonyl residue —COO—$R^{12}$ or particularly preferably a sulfonyl residue —$SO_2R^{12}$,
$R^{12}$ denotes H, a branched or unbranched, substituted or unsubstituted alkyl, alkenyl, alkinyl, aryl or heteroaryl residue or a substituted or unsubstituted cyclic alkylresided or a substituted or unsubstituted aralkyl, alkylaryl or heteroaralkyl residue or a substituted or unsubstituted bicyclic or polycyclic residue,
$R^{15}$ represents $C=X^2$, $NR^3$ or $CR^3{}_2$,
n is an integer from 0 to 2,
m is an integer from 0 to 5,
o is an integer from 1 to 5,
or salts of these compounds.

8. The method according to claim 7 further comprising administering at least one further pharmaceutically active ingredient suitable for the treatment of the bacterial meningitis.

9. The method according to claim 1 further comprising administering at least one further pharmaceutically active ingredient suitable for the treatment of the neurodegenerative disease.

* * * * *